(12) United States Patent
Schmidlin (10) Patent No.: US 10,470,850 B2
(45) Date of Patent: Nov. 12, 2019

(54) RE-STERILIZATION BY RECOATING THE INFECTED IMPLANT USING A SLEEVE

(71) Applicant: UNIVERSITAT ZURICH, Zurich (CH)

(72) Inventor: Patrick Schmidlin, Oberdurnten (CH)

(73) Assignee: UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 15/737,288

(22) PCT Filed: Jun. 18, 2016

(86) PCT No.: PCT/EP2016/064108
§ 371 (c)(1),
(2) Date: Dec. 17, 2017

(87) PCT Pub. No.: WO2016/203033
PCT Pub. Date: Dec. 22, 2016

(65) Prior Publication Data
US 2018/0153657 A1   Jun. 7, 2018

(30) Foreign Application Priority Data

Jun. 18, 2015 (EP) .................................. 15172786

(51) Int. Cl.
*A61C 8/00* (2006.01)
*A61C 19/06* (2006.01)

(52) U.S. Cl.
CPC .............. *A61C 8/0013* (2013.01); *A61C 8/00* (2013.01); *A61C 8/0039* (2013.01); *A61C 8/0089* (2013.01); *A61C 19/06* (2013.01)

(58) Field of Classification Search
CPC ....... A61C 8/0013; A61C 8/00; A61C 8/0039; A61C 8/0089; A61C 19/06
See application file for complete search history.

(56) References Cited

U.S. PATENT DOCUMENTS 5,782,635 A * 7/1998 Altvater ............... A61C 17/036
433/143
6,840,770 B2 * 1/2005 McDevitt ............. A61C 8/0033
433/173

(Continued)

FOREIGN PATENT DOCUMENTS

DE    2540077    4/1976
EP    1522271    4/2005

(Continued)

*Primary Examiner* — Ralph A Lewis
(74) *Attorney, Agent, or Firm* — JMB Davis Ben-David (57) ABSTRACT

The invention relates to a sleeve (1) for providing a dental implant (2) with a disinfectable surface (100*b*), wherein the sleeve (1) is configured to be attached to an end or coronal region (20) of a dental implant (2), wherein the sleeve (1) comprises a through hole (101) encompassed by the sleeve (2) which through hole (101) is adapted to receive said end region (20) of the dental implant (2), wherein said through hole (101) is delimited by an inside (100*a*) of the sleeve which faces said through hole (101), and wherein the sleeve (1) comprises an outside (100*b*) facing away from said inside (100*a*), which outside (100*b*) forms said disinfectable or sterilizable surface (100*b*). Further, the invention relates to an arrangement of the sleeve on a dental implant as well as to a method for arranging the sleeve on a dental implant.

15 Claims, 5 Drawing Sheets

(56) References Cited

U.S. PATENT DOCUMENTS

| | | | |
|---|---|---|---|
| 7,179,084 B1* | 2/2007 | Kometas | A61C 8/0089 |
| | | | 433/165 |
| 9,333,054 B1* | 5/2016 | Garfinkel | A61C 8/0009 |
| 2009/0036908 A1* | 2/2009 | Zokol | A61B 17/60 |
| | | | 606/151 |
| 2009/0286202 A1 | 11/2009 | Ford et al. | |
| 2010/0291506 A1* | 11/2010 | Olsson | A61C 8/0089 |
| | | | 433/143 |
| 2012/0156645 A1 | 6/2012 | Jacoby | |
| 2014/0137345 A1* | 5/2014 | Kim | A46B 9/02 |
| | | | 15/22.1 |

FOREIGN PATENT DOCUMENTS

| | | |
|---|---|---|
| JP | H03292949 | 12/1991 |
| KR | 20110111181 | 10/2011 |
| WO | 2015/112482 | 7/2015 |

\* cited by examiner

RE-STERILIZATION BY RECOATING THE INFECTED IMPLANT USING A SLEEVE

CROSS-REFERENCE TO RELATED APPLICATIONS

This is the U.S. National Stage of International Application No. PCT/EP2016/064108 filed Jun. 18, 2016, which was published in English under PCT Article 21(2), and which in turn claims the benefit of European Patent Application No. 15172786.4 filed Jun. 18, 2015.

The invention relates to a sleeve for a dental implant, and arrangement involving a sleeve and a dental implant as well as a method for arranging a sleeve on a dental implant, as well as a system comprising a sleeve according to the invention and a drill head.

Dental implants have become a routine intervention to replace missing teeth in dentistry and represent an ideal prosthetic solution nowadays to replace missing roots when ideally placed in jaws of adequately selected patients. Over the last decades, these implant solutions therefore became very successful options in oral rehabilitation and offer dentists and patients a variety of treatment options. Recent data suggest very low rates of biologic and technical complications in these selected patients with more or less ideal conditions and under good maintenance conditions. However, in patients with increased risk such as smokers, or patients with a history of periodontitis and less ideal oral hygiene, or in patients with systemic diseases, implants show distinctly more often problems, which may reflect more the clinical reality. Among the investigated complications with implants, mucositis and peri-implantitis seem to be the most prevalent diseases when in function. Peri-implantitis represents an inflammatory disease, which affects the marginal soft and hard tissues surrounding osseointegrated implants. Already twenty years ago, a cause-effect relationship between bacterial plaque accumulation and inflammatory changes in the soft tissues surrounding dental implants has been proven under clinical conditions. And the formation of oral biofilms seems to be a defining factor for the success or the failure of dental implants and is accepted as a primary causative factor by the scientific community. Clinical manifestations, such as mucositis with gingival bleeding and swelling and peri-implantitis with additional bone loss and maybe pus secretion, highly resemble periodontal inflammations and—as mentioned above—microbial colonization is the key etiological factor in both diseases. Then as soon as an implants are exposed to the oral environment, bacterial colonization begins. Not surprisingly, biofilms on implant surfaces are quite similar in composition and structure as those on teeth, but may be additionally influenced by the implant's special micro- and macroscopic design features. Especially the coronal portion surface of an implant can become undesirably exposed to the oral cavity and may facilitate plaque accumulation, which consequently can lead to more progressive inflammatory reactions.

The main problem in successfully treating peri-implantitis is the fact that it is merely impossible to perfectly clean the infected surface. To date, it is not known, to what extent it is necessary to disinfect or (re-)sterilize the surface of teeth or implants to allow for adequate healing or regeneration. We know from teeth, for example, that there exists a so-called "residual calculus parodox", which means that despite persisting debris on the root surface the body can overcome the challenge of the remaining bacteria and calcified deposits and heal. However, one must take into consideration that this healing under such conditions does not correspond to regeneration but rather to a formation of a long junctional epithelium. In implants, a re-osseointegration is less likely. Despite evidence showing that peri-implant lesion may be partially resolved and further bone loss may be prevented following a treatment regimen that includes systemic administration of antibiotics and local antimicrobial therapy. Whereas some bone regrowth may occur in the periphery of the previous lesion, a predominantly dense fibrous capsule forms next to the exposed fixture surface and it was generally concluded that re-osseointegration to previously contaminated but cleaned and conditioned titanium surfaces is difficult if not impossible. This statement has still not been rejected by alternative treatment regimens or optimized. Persson and co-workers, however, proved in a unique preclinical study the concept that the quality of the titanium surface is indeed of decisive importance for both osseointegration and re-osseointegration (Persson et al., 2001). For this purpose, Persson and coworkers [Persson LG. Ericsson I, Berglundh T, Lindhe J: Osseintegration following treatment of peri-implantitis and replacement of implant components. An experimental study in the dog. J Clin Periodontol 2001; 28: 258-263] created custom-made fixtures consisting of 6-mm long apical and 4-mm long coronal parts connected with an internal screw. After 4 months, abutment connection was performed. Five months later, a period of experimental peri-implantitis was initiated during which about 50% of the supporting bone tissue was lost. The experimental animals, Labrador dogs, were later subjected to either a treatment that included (i) systemic administration of antibiotics or (ii) a surgical debridement of all implant sites. The abutments and the coronal parts of the text fixtures were removed. All parts of the exposed portion of the standard fixtures, the connecting screw and the apical part of the test fixtures were meticulously cleaned by mechanical means. A pristine, coronal fixture part via the connecting screw was attached to the apical fixture part of each test fixture. All fixtures were submerged. Results demonstrated that re-osseointegration failed to occur to implant surfaces exposed to bacterial contamination, but did consistently occur at sites where a new implant component was placed in the bone defect after surgical debridement.

Therefore, the problem underlying the present invention is to provide a device, an arrangement and a method that promotes reintegration of tissue according the biological concept of re-integration and adaptation of tissues on sterile surfaces, i.e. bone and soft tissue, leading particularly to re-osseointegration as the ultimate goal of the original tissue integration.

This problem is solved by a sleeve having the features of claim 1.

According thereto, a sleeve, preferably for providing a dental implant with a new, disinfectable or sterilizable surface, is disclosed, wherein the sleeve is configured to be attached to the coronal region of a dental implant, wherein the sleeve comprises a through hole encompassed by the sleeve, which through hole is adapted to receive said end or coronal portion of the dental implant, wherein said through hole is delimited by an inside of the sleeve which faces said through hole, and wherein the sleeve comprises an outside facing away from said inside, which outside preferably forms said disinfectable or sterilizable surface.

Particularly, in other words, the current invention follows the principle of cleaning the contaminated surface following actual standards and then sealing this surface and re-coating it with the sleeve. Advantageously, the latter allows for tissue re-integration (bone and soft tissues) using guided bone re-integration (GBR) techniques and a later re-restoration.

Particularly, in the context of the present invention, a dental implant is a surgical component that is configured to interface with the bone of the jaw or skull of a patient to support a dental prosthesis such as a crown, bridge, denture, facial prosthesis or to act as an orthodontic anchor.

According to an embodiment of the present invention, said inside of the sleeve comprises at least one of: a thread forming e.g. an inner thread of the sleeve, a surface structure, a sand-blasted surface, that is particularly obtained by sandblasting the surface (e.g. with sand or other suitable abrasive particles). Further, according to an embodiment of the sleeve according to the invention, said thread comprises a left-hand thread and a right-hand thread intersecting with each other.

Further, according to an embodiment of the sleeve according to the invention, said outside comprises at least one of: a coating, a coating comprising an osseointegrative material, an osseointegrative material, a chemically treated surface, a sand-blasted surface, a biologically activated surface (e.g. for an accelerated and improved healing of an implant), a macro-structure for improving osseointegration, particularly windings, steps, or protrusions (see also below). Preferably, in case said outside comprises titanium (Ti) or is formed out of titanium, said outside surface is mechanically roughened (particularly by sandblasting it) and/or chemically etched. Further, said outside may also be anodized.

In the context of the present invention, osseointegration is defined as a formation of a direct interface between an implant (i.e. the sleeve) and a bone, without intervening soft tissue. Particularly, an osseointegrative outside/surface comprises pores into which osteoblasts and supporting connective tissue can migrate.

Further, according to an embodiment of the sleeve according to the invention, the sleeve and/or said outside of the sleeve is formed out of or comprises one of the following materials: platinum, zirconium, PEEK or any other relevant material, which can be used in dental technology.

Further, according to an embodiment of the sleeve according to the invention, said outside comprises a cylindrical portion extending up to a first face side of the sleeve forming a first end of the sleeve. Particularly, the sleeve and said outside extend along an axial direction (e.g. longitudinal or cylinder axis of the sleeve).

Further, according to an embodiment of the sleeve according to the invention, the sleeve comprises a second face side, which forms a second end of the sleeve. Particularly said face sides face away from each other and form boundary regions delimiting the through hole of the sleeve on either side.

Further, according to an embodiment of the sleeve according to the invention, the sleeve is designed to be arranged on said end region of the dental implant with the second end ahead.

Further, according to an embodiment of the sleeve according to the invention, the sleeve comprises a circumferential region adjacent said second face side, which second region is tapered towards the second face side.

Further, according to an embodiment of the sleeve according to the invention, the sleeve comprises a plurality of annular protrusions adjacent said second end of the sleeve (i.e. the apical part/region of the sleeve), which protrusions protrude radially from said outside.

Further, according to an embodiment of the sleeve according to the invention, said protrusions form a portion of said outside having a toothed structure.

The benefit of such a structure is an improved retention of an implant to be attached to the sleeve.

According to a further aspect of the present invention, an arrangement is disclosed, the arrangement comprising a dental implant and a sleeve according to the invention, wherein the dental implant is inserted into the through hole of the sleeve with an end region of the dental implant, and wherein the sleeve is attached to the dental implant by means of a connection means.

Preferably, said connection means is one of or comprises one of: a positive connection means (e.g. using a form-locked connecting element), a force-fit connection means (e.g. using a force-locked connection element), a connection means based on friction, an adhesive, particularly a cement, particularly a biocompatible cement or adhesive (e.g. a cement or adhesive having the quality of not having toxic or injurious effects on biological systems). Of course, these connection means may also be combined.

According to an embodiment of the present invention, said cement or adhesive is formed by or comprises one of the following substances: intermediate restorative materials (IRM), glass ionomer cement materials (GIC), mineral troxide aggregates (MTA), etc.

According to an embodiment of the present invention, said cement or adhesive preferably is a resorbable cement, e.g. comprising natural or synthetic degradable polymers, which preferably harden in situ, e.g. polylactic acid, and which are preferably applied by ultrasonic assisted or chemical means.

Preferably, said cement or adhesive is at least arranged in a circumferential gap between the dental implant and the inside of the sleeve.

Further, according to an embodiment of the arrangement according to the invention, said biocompatible cement is formed by or comprises one of the following substances: glass-ionomer cements, mineral trioxide aggregate, bone cements, etc.

Further, according to an embodiment of the present invention, the sleeve is fabricated using CAD/CAM technology, e.g. by using Scanbodies or Scanposts. Particularly, a Scanbody or Scanpost is a little piece, which is placed into the implant and determines the position and orientation of the implant as well as the inner configuration of the implant during the scanning and allows for the alignment of the designed CAD/CAM restoration. Preferably, the sleeve will then be fabricated using CAD/CAM technology using titanium, zirconium, PEEK or another material, which is suitable for its indirect fabrication.

This approach would allow for the fabrication of sleeves with integrated crowns chair-side or indirect in the laboratory, which are then sterilized or disinfected and mounted on the implant, e.g. as described herein, or particularly by cementation or screw-retention or a combination thereof.

Accordingly, in a further embodiment of the present invention, the sleeve comprises an integrated crown.

According to a further aspect of the present invention, a system is disclosed, wherein the system comprising a sleeve according to one of the preceding claims and a drill head having an opening that is configured to receive an end portion of the dental implant upon removing by means of said drill head a protruding portion of the dental implant that protrudes from said end portion, such that the end portion of the dental implant can be inserted into the through hole of the sleeve.

Further according to an embodiment, the system may comprise a drilling device comprising said drill head, wherein the drilling device may be configured to rotate, oscillate, and/or vibrate in order to remove said protruding portion.

Further, according to an embodiment, the opening of the drill head is delimited by a circumferential inner abrasive surface of the drill head that is configured to remove said protruding portion, wherein said abrasive surface may be formed by a diamond coating or other internal machining/coating of said inner surface, which allows adequate abrasion of the implant material without causing extensive heat development. Further, the drill head comprises an abrasive edge region delimiting said opening of the drill head so that the drill head also enables an apical drilling action for removal of e.g. 1 mm to 2 mm bone in order to allow for a proper seating of the sleeve in the healthy bone tissue if desired.

Further, according to an embodiment, the drilling device comprise a cooling means for cooling the drill head, wherein particularly the cooling means is configured use water as a coolant.

According to a further aspect of the present invention, a method for fixing a sleeve according to the invention to a dental implant for providing the dental implant with a new disinfectable or sterilizable surface is disclosed, wherein the method comprises the steps of:
- arranging the sleeve on the end region of the dental implant so that said end region is inserted into said through hole of the sleeve,
- and fastening the sleeve to the dental implant by means of a connection means.

Said connection means can be one of the above described connection means. As described above, an adhesive or cement is preferably arranged in a circumferential gap between the dental implant and the inside of the sleeve.

According to an embodiment, the sleeve is fastened to the dental implant by means of a connection means in the form of an adhesive or cement (e.g. see also above) which is applied to said end region of the dental implant and/or to said inside of the sleeve, before the sleeve is arranged on the end region of the dental implant.

Further features and advantages of the invention shall be described by means of a detailed description of an embodiment with reference to the Figures, wherein FIG. 1 shows in conjunction with FIGS. 2 to 4 a sleeve 1 according to the invention.

The sleeve 1 allows providing a dental implant 2 with a fresh, disinfectable or sterilizable surface 100b in order to promote bone re-integration into the sleeve 1/dental implant 2. For this, the sleeve 1 is configured to be attached to an end or coronal region 20 of the dental implant 2, which in turn comprises e.g. an outer thread 21 for connecting the dental implant to a bore hole in a bone.

Further, the sleeve 1 comprises a through hole 101 defined by the sleeve 2, which through hole 101 is designed to receive said end region 20 of the dental implant 2 with a small play (i.e. a gap between the sleeve and the end region of the dental implant may lie within the range from 2 mm to 15 mm), wherein said through hole 101 is delimited by an inside 100a of the sleeve 1, which inside 100a faces said through hole 101, and wherein the sleeve 1 comprises an outside 100b facing away from said inside 100a, which outside 100b forms said disinfectable surface 100b that is to be provided.

Figure 2:
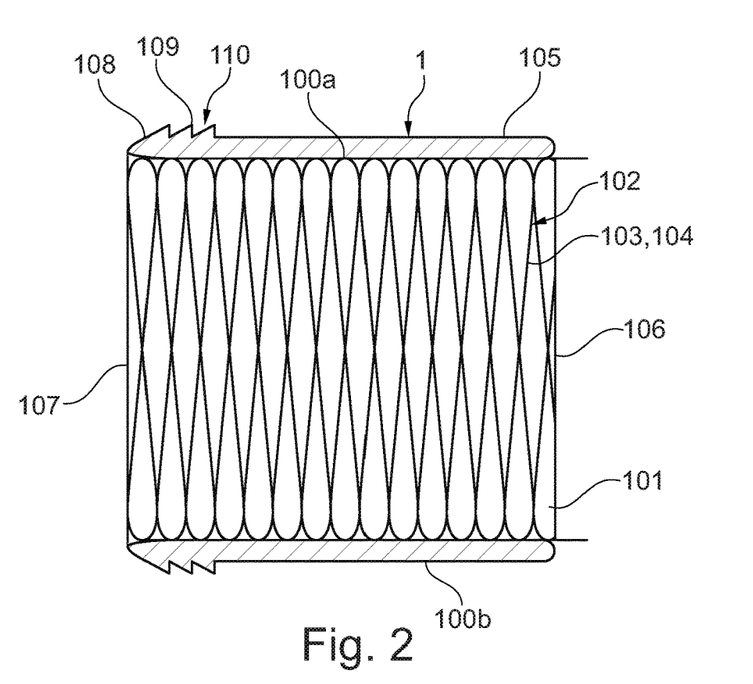
FIG. 2 shows a cross-sectional view of the sleeve as indicated in FIG. 3.

Further, said inside may comprises a thread 102, e.g. in the form of an intersecting left and right hand thread 103, 104. Other surface modifications, e.g. as described herein, are also possible (e.g. sandblasting, coatings etc.)

Preferably, said outside 100b comprises an osseointegrative material or is formed by an osseointegrative material in order to promote osseointegration of the bone into the outside 100b of the sleeve. For this, the sleeve or said outside 100b may be formed out of platinum, zirconia, PEEK or another suitable material.

Figure 1:
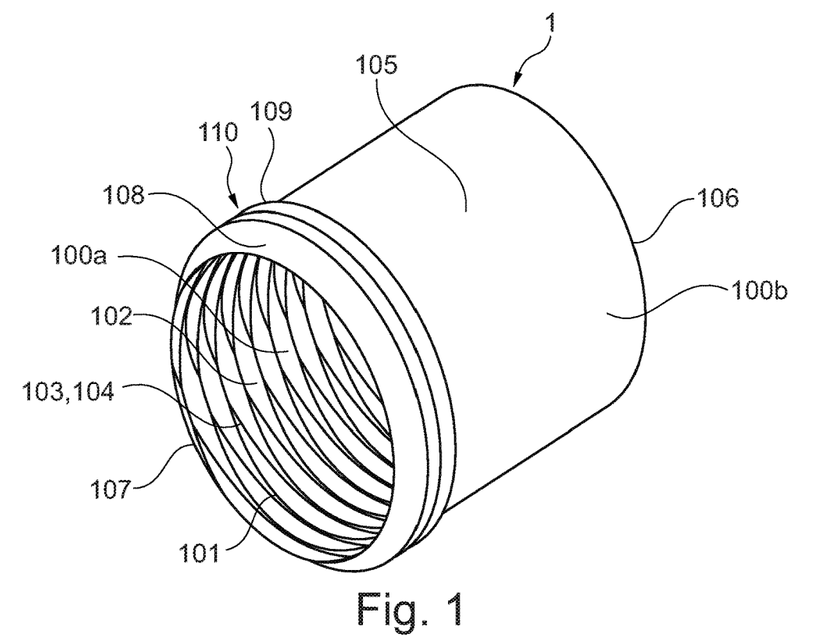
FIG. 1 shows a perspective view of a sleeve according to the invention.
Figure 3:
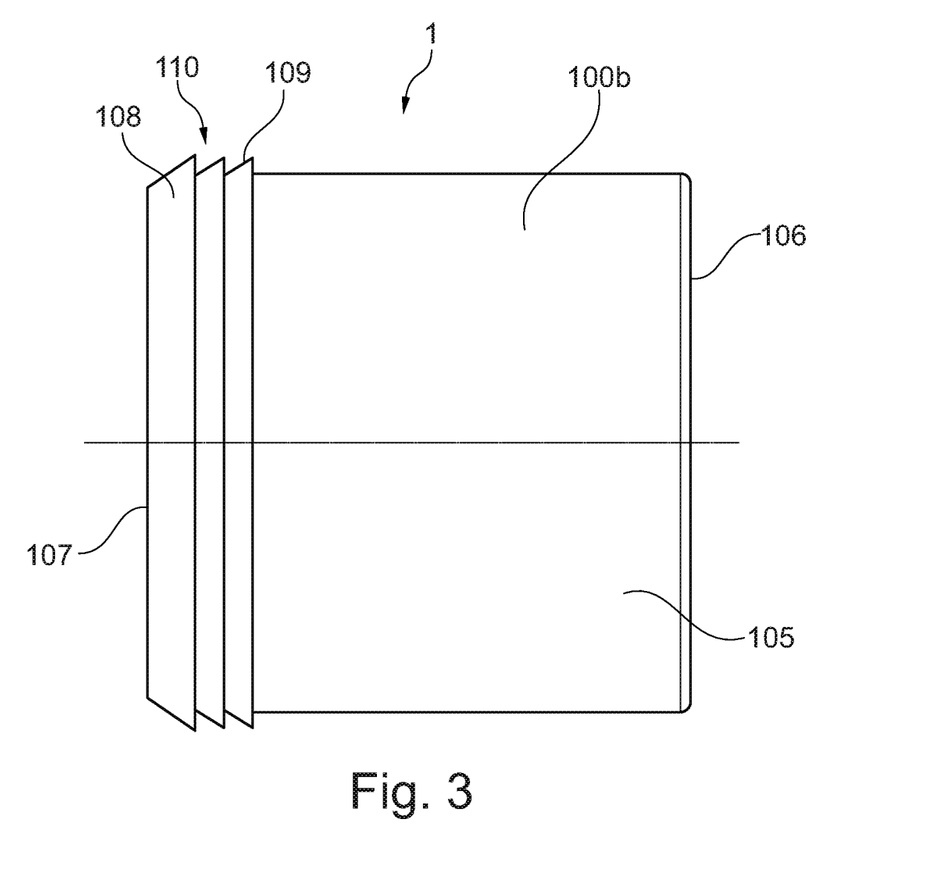
FIG. 3 shows a lateral view of the sleeve.

Further said outside 100b preferably forms a cylindrical portion 105 extending in the axial direction of the sleeve 1 up to a circumferential first face side 106 of the sleeve 1 which forms a first end of the sleeve 1 as well as an edge of the through hole 101. On the other opposing (second) end of the sleeve, the sleeve comprises a second circumferential face side, which faces away from the first face side and also forms an edge of the through hole 101 that extends through the sleeve in the axial direction of the sleeve.

Figure 4:
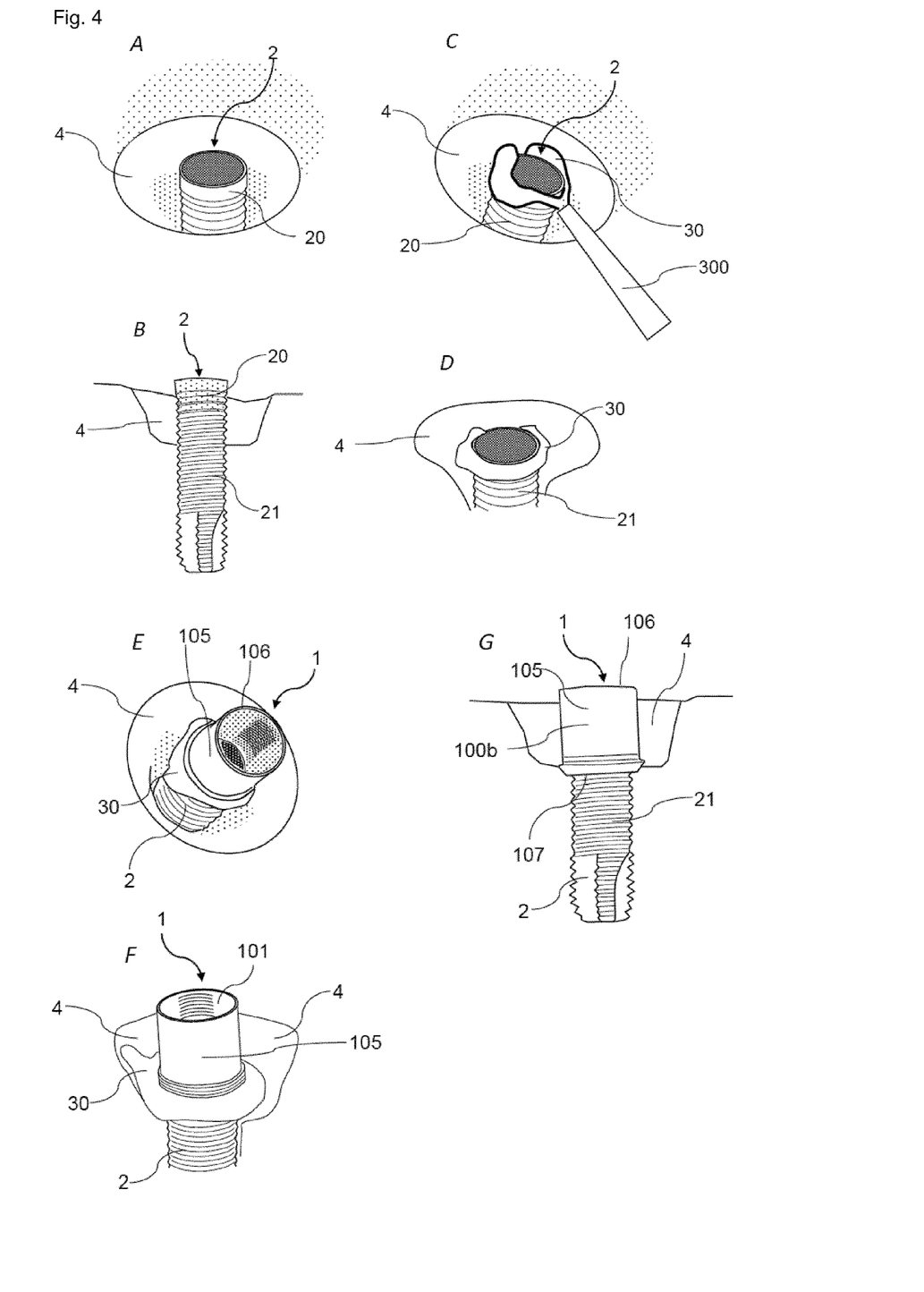
FIG. 4 shows the placement of a sleeve according to the invention on a dental implant.

Preferably, the sleeve 1 is designed to be put over said end region 20 of the dental implant 2 with the second end ahead as is shown in FIG. 4 A to G.

Furthermore, the sleeve 1 comprises a circumferential region 108 adjacent said second face side 107, which circumferential region 108 can be tapered towards the second face side 107.

Further, the sleeve 1 may comprises a plurality of annular protrusions 109 adjacent said second end 107, which protrusions 109 project radially from said outside 100b of the sleeve and thereby form a portion 110 of said outside 100b of the sleeve 1 having a toothed structure.

In order to arrange the sleeve 1 on a dental implant 2 as shown in FIG. 4 A to G, a surgical approach may be used beforehand. Here, a flap is raised under local anesthesia and inflamed tissues are removed. Preferably, a flapless procedure/surgery is employed or a nonsurgical approach, which allows the placement of the sleeve (e.g. when using electric current for the disinfection of the implant surface).

Preferably, since the bone defects will be exposed the implant surfaces are thoroughly cleaned, particularly by the most appropriate state of the art method available (e.g. antimicrobial solutions, lasers, mechanical debridement, etc.).

If necessary, depending on the individual implant anatomy, a so-called implantoplasty is performed. This means that the neck of the dental implant is reshaped or parallelized in order to allow the insertion of the prefabricated sleeve 1. This may be necessary especially for tulip-form implant types or implants with distinct thread designs.

Implantoplasty represent already a common treatment form in surgical peri-implant therapy. However, it is invasive and creates unwanted debris in form of small titanium particles, which may be problematic in wounds. If this treatment could be reduced to a minimum in the most coronal aspects of the implant only this would represent a significant advantage already.

Advantageously, the placement of the sleeve 1 is simple. Particularly, after a defect preparation, disinfection and possibly try-in, a cementum 30 is placed on the implant surface 20 (using e.g. a syringe 300) and in the sleeve 1 is placed on the end region 20 of the dental implant 2 (cf. FIG. 4 panels A to F) After initial setting, excess material can be easily removed and the placement can be finished.

After placement of the sleeve 1, the defect can be either filled with e regenerative material and a membrane can be placed (GBR; guided bone regeneration) or the flap can be closed and the tissue can heal without regeneration (FIG. 4 panel G). The specific healing intentions depend mainly on the specific defect morphologies and the individual treatment plan.

The use of a cementum 30 can be a special feature when using the sleeve 1. Therefore, in vitro experiments were conducted to assess the bonding potential of machined titanium (smooth) to commercially available cements to prove the principle that there is adherence between the two components (even to smooth and not even rough titanium). Samples were store 24 h at 37° C. before shear bond strength measurements were taken (MPa) which are shown in FIG. 5.

Bone cements, which are already used in orthopedics, were chosen (Biomet 3i). One of them contained antibiotics, which is conceptually ideal for peri-implantitis. In addition, other agents can be considered which are used in dentistry, such as IRM (intermediate resotrative materials), GIC (glass ionomer cement materials), MTA (mineral troxide aggregate), etc.

One may also consider and adapt other materials from general orthopedic surgery.

Figure 5:
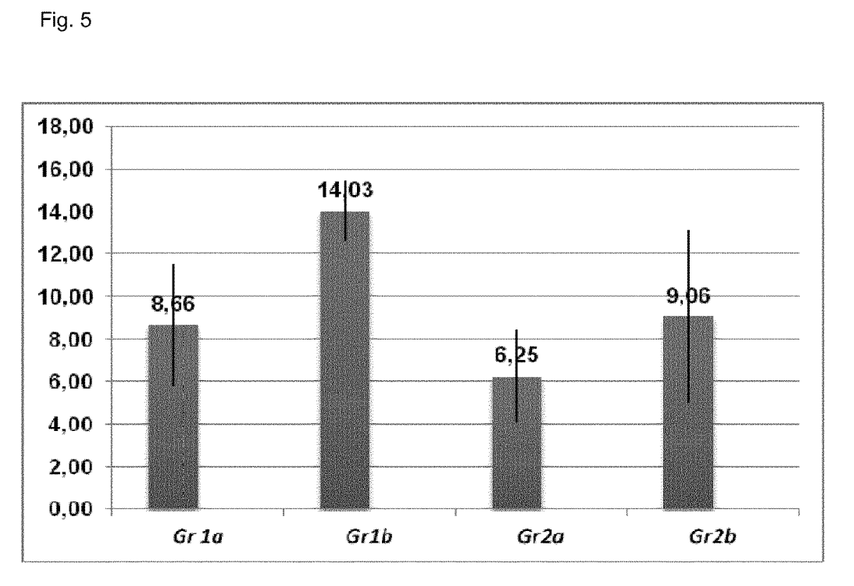
FIG. 5 shows shear bond strength of four different cement connections connecting a sleeve according to the invention to a dental implant.

In detail, FIG. 5 shows the shear bond strength for four different groups:

Group 1 a: Titanium-Bone cementum (Refobacin bone cementum) without air-abrasion.

Group 1 b: Titanium-Bone cementum (Refobacin bone cementum) with air-abrasion.

Group 2a: Titanium-Bone cementum (Refobacin plus Clindamicin) without air-abrasion.

Group 2b: Titanium-Bone cementum (Refobacin plus Clindamicin) with air-abrasion.

Figure 6:
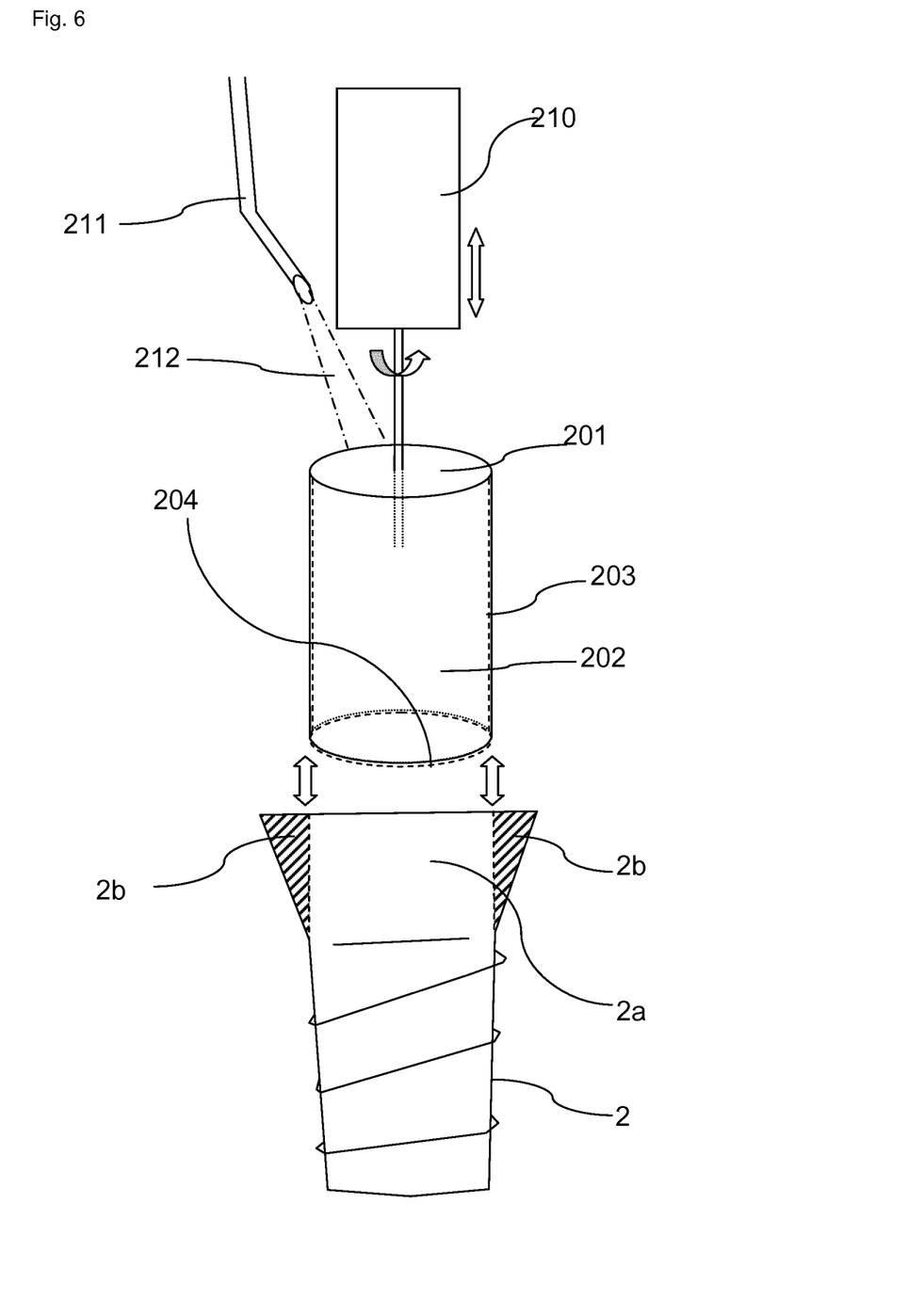
FIG. 6 shows a drill head and drilling device adapted to the sleeve according to the invention

Furthermore, as illustrated in FIG. 6, the application of the sleeve 1 may require the parallelization of the dental implant 2 in one or more aspects if necessary. This means the potential removal of the coronal aspect where a crown is mounted (i.e. the abutment area) in cases of implants with a tulip or step configuration or the modification of the implant body of tapered implants or implants with excessive threads. According to the embodiment shown in FIG. 6 a drill head 201 in the form of a hollow burr is provided which comprises an opening 202 delimited by a circumferential inner abrasive surface 203, which opening 202 fits the size of the sleeve 1 and removes the above-mentioned macrostructures, e.g. protruding portions (also called aspects) 2a that protrude (e.g. laterally) from the proper end region 2a of the implant 2.

The action of a drilling device 210 for driving the drill head 201 can be either rotating, oscillating or vibrating, and preferably comprises a cooling means 211 that is preferably configured to provide a water-cooling 212 of the drill head 201. The grinding action of the inner surface 203 is preferably achieved by a diamond-coating or other internal machining/coating of said surface 203, which allows adequate abrasion of the implant material without causing extensive heat development.

The drill head 201 may further comprise an apical drilling action to allow for some removal of 1-2 mm bone in order to allow for a proper seating of the sleeve 1 in the healthy bone tissue. This may be provided by an abrasive edge region 204 of the drill head 201.

The invention claimed is:

1. A sleeve (1) for providing a dental implant (2) with a disinfectable or sterilizable surface (100b), wherein the sleeve (1) is configured to be attached to an end or coronal region (20) of a dental implant (2),
   wherein the sleeve (1) comprises a through hole (101) encompassed by the sleeve (2) which through hole (101) is adapted to receive said end or coronal region (20) of the dental implant (2),
   wherein said through hole (101) is delimited by an inside (100a) of the sleeve which faces said through hole (101), and
   wherein the sleeve (1) comprises an outside (100b) facing away from said inside (100a), which outside (100b) forms said disinfectable or sterilizable surface (100b), and
   wherein said inside comprises a sand-blasted surface or a thread (102) that comprises a left-hand thread (103) and a right-hand thread (104) intersecting with the left-hand thread (103).

2. The sleeve according to claim 1, characterized in that said outside (100b) comprises at least one of: a coating, a coating comprising an osseointegrative material, an osseointegrative material, a mechanically treated surface, a chemically treated surface, a biologically activated surface, a macro-structure for improving osseointegration.

3. The sleeve according to claim 2, characterized in that the macro-structure for improving osseointegration is in the form of one of: windings, steps, pits, grooves.

4. The sleeve according to claim 1, characterized in that the sleeve (1) and/or said outside (100b) of the sleeve (1) is formed out of or comprises one of the following materials: platinum, zirconium, PEEK.

5. The sleeve according to claim 1, characterized in that said outside (100b) comprises a cylindrical portion (105) extending up to a first face side (106) of the sleeve (1) forming a first end of the sleeve.

6. The sleeve according to claim 1, characterized in that the sleeve (1) comprises a second face side (107), which forms a second end of the sleeve (1).

7. The sleeve according to claim 6, characterized in that the sleeve (1) is designed to be put over said end region (20) of the dental implant (2) with the second end ahead.

8. The sleeve according to claim 6, characterized in that the sleeve (1) comprises a circumferential region (108) adjacent said second face side (107), which circumferential region (108) is tapered towards the second face side (107).

9. The sleeve according to claim 6, characterized in that the sleeve (1) comprises a plurality of circumferentially extending protrusions (109) adjacent said second end, which protrusions protrude radially from said outside (100b).

10. The sleeve according to claim 9, characterized in that said protrusions (109) form a portion of said outside (100b) having a toothed structure (110).

11. An arrangement comprising a dental implant (2) and a sleeve (1) according to claim 1,
   wherein the dental implant (2) is inserted into the through hole (101) of the sleeve (1) with an end region (20) of the dental implant (2), and
   wherein the sleeve (1) is fastened to the dental implant (2) by means of a connection means.

12. The arrangement according to claim 11, characterized in that said connection means is one of or comprises one of: a positive connection means, a force-fit connection means, an adhesive.

13. The arrangement according to claim 12, characterized in that the adhesive is one of: a cement, a biocompatible cement, a biocompatible adhesive.

14. System comprising a sleeve (1) according to claim 1 and a drill head (201) having an opening (202) that is configured to receive an end region (2a) of the dental implant (2) upon removing by means of said drill head (201) a protruding portion (2b) of the dental implant (2) that protrudes from said end region (2a), such that the end region (2a) of the dental implant (2) can be inserted into the through hole (101) of the sleeve (1).

15. Method for fixing a sleeve according to claim 1, to a dental implant (2) for providing the dental implant (2) with a disinfectable or sterilizable surface (100b), wherein the method comprises the steps of:
  arranging the sleeve (1) on the end region (20) of the dental implant (2) so that said end region (20) is inserted into said through hole (101) of the sleeve (1), and
  fixing the sleeve (1) to the dental implant (2) by means of a connection means (30).

* * * * *